United States Patent
Griffin et al.

(10) Patent No.: US 8,377,112 B2
(45) Date of Patent: *Feb. 19, 2013

(54) SACRIFICIAL ANODE STENT SYSTEM

(75) Inventors: Stephen Griffin, Sunnyvale, CA (US); Brent C. Gerberding, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/227,202

(22) Filed: Sep. 7, 2011

(65) Prior Publication Data

US 2011/0319928 A1    Dec. 29, 2011

Related U.S. Application Data

(63) Continuation of application No. 11/121,027, filed on May 3, 2005, now Pat. No. 8,016,853, which is a continuation of application No. 10/180,706, filed on Jun. 26, 2002, now abandoned.

(51) Int. Cl.
*A61F 2/82* (2006.01)

(52) U.S. Cl. ............ 623/1.15; 623/1.34; 623/1.11; 606/200

(58) Field of Classification Search ............ 606/198, 606/108, 200, 151, 231, 194, 32; 623/1.11, 623/1.12, 1.13, 1.1, 11.11, 903; 128/898
See application file for complete search history.

(56) References Cited

U.S. PATENT DOCUMENTS

| | | | |
|---|---|---|---|
| 4,776,337 A | 10/1988 | Palmaz | |
| 4,994,069 A | 2/1991 | Ritchart et al. | |
| 5,091,205 A | 2/1992 | Fan | |
| 5,122,136 A | 6/1992 | Gugleilmi et al. | |
| 5,360,440 A * | 11/1994 | Andersen | 607/115 |
| 5,423,829 A | 6/1995 | Pham et al. | |
| 5,522,822 A | 6/1996 | Phelps et al. | |
| 5,643,254 A | 7/1997 | Scheldrup et al. | |
| 5,725,572 A | 3/1998 | Lam et al. | |
| 5,741,327 A | 4/1998 | Frantzen | |
| 5,795,318 A * | 8/1998 | Wang et al. | 604/8 |
| 5,837,907 A | 11/1998 | Ohmi et al. | |
| 5,873,907 A | 2/1999 | Frantzen | |
| 5,922,021 A | 7/1999 | Jang | |
| 5,938,695 A | 8/1999 | Borghi | |
| 5,951,599 A | 9/1999 | McCrory | |
| 5,984,929 A * | 11/1999 | Bashiri et al. | 606/108 |
| 6,007,573 A | 12/1999 | Wallace et al. | |
| 6,019,877 A * | 2/2000 | Dupelle et al. | 204/196.11 |
| 6,024,754 A | 2/2000 | Engelson | |
| 6,059,779 A | 5/2000 | Mills | |
| 6,096,034 A | 8/2000 | Kupiecki et al. | |
| 6,123,714 A * | 9/2000 | Gia et al. | 606/151 |
| 6,187,015 B1 | 2/2001 | Brenneman | |
| 6,189,536 B1 * | 2/2001 | Martinez et al. | 128/897 |
| 6,203,568 B1 | 3/2001 | Lombardi et al. | |
| 6,348,065 B1 | 2/2002 | Brown et al. | |
| 6,379,373 B1 | 4/2002 | Sawhney et al. | |
| 6,663,607 B2 | 12/2003 | Slaikeu et al. | |
| 6,896,696 B2 | 5/2005 | Doran | |
| 2004/0002752 A1 | 1/2004 | Griffin | |

FOREIGN PATENT DOCUMENTS

EP    739607    4/1996

* cited by examiner

*Primary Examiner* — Elizabeth Houston
(74) *Attorney, Agent, or Firm* — Vidas, Arrett and Steinkraus

(57) ABSTRACT

A sacrificial anode stent system comprises a stent having at least one sacrificial anode portion and a vaso-occlusive device. The vaso-occlusive device has at least one portion with a potential different from that of the sacrificial anode portion of the stent.

20 Claims, 3 Drawing Sheets

SACRIFICIAL ANODE STENT SYSTEM

CROSS-REFERENCE TO RELATED APPLICATIONS

Figure 1:
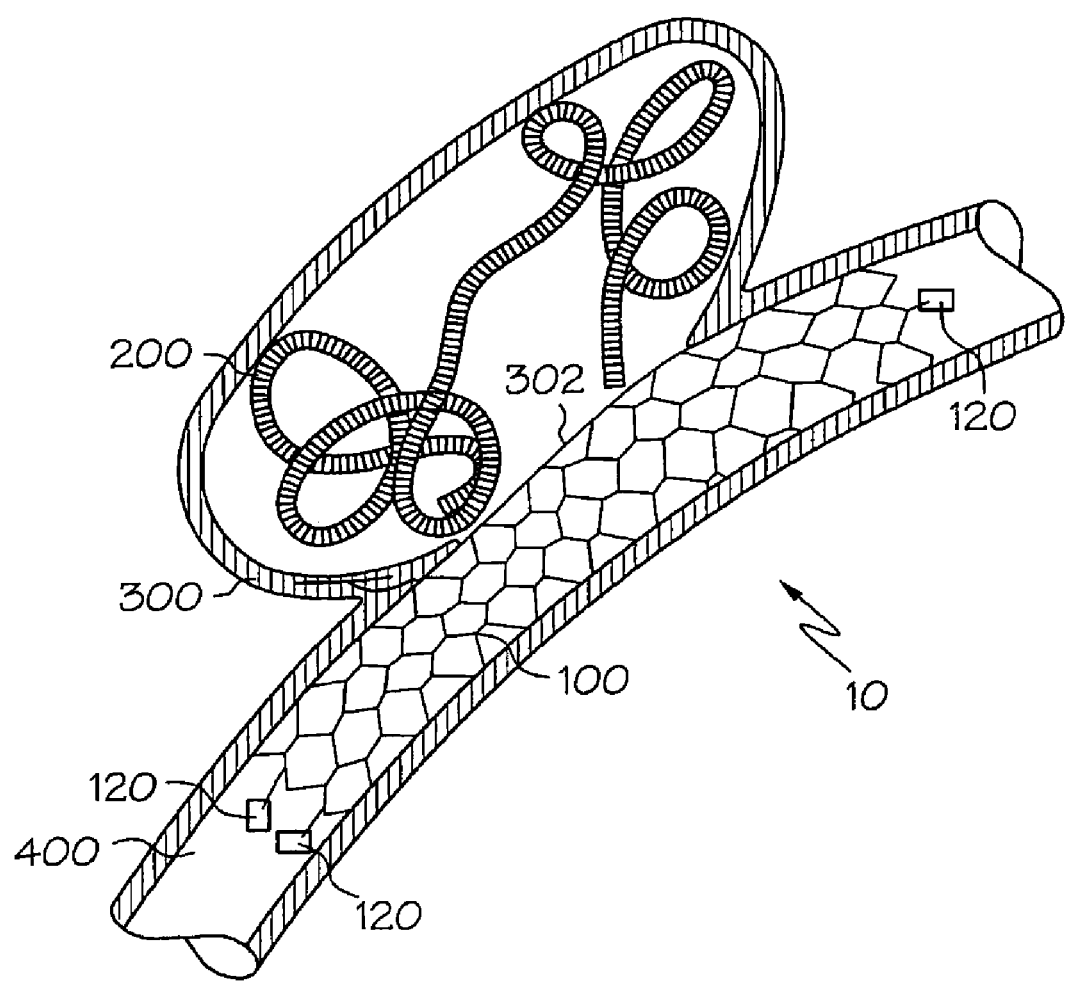

This application is a Continuation application of application Ser. No. 11/101,027, filed May 3, 2005 which is a Continuation application of application Ser. No. 10/180,706, filed Jun. 26, 2002, the contents of each of which are hereby incorporated by reference.

FIELD OF INVENTION

The present invention relates generally to implantable devices and methods for the non-invasive treatment of vascular defects such as an aneurysm.

BACKGROUND OF THE INVENTION

An aneurysm may generally be described as a weakening in the wall of an artery or vein resulting in a bulge or bubble protruding in a radial direction relative to the adjacent vessel wall.

In the past, aneurysms have been treated through a procedure which surgically clips an aneurysm shut with a metal clip. Alternatively, the neck of the aneurysm may be clipped followed by a suture ligation of the neck of the aneurysm or the wrapping of the entire aneurysm. Each of these surgical procedures constitutes an intrusive invasion into the body for which certain areas of the body such as the brain have little tolerance. An aneurysm left untreated may rupture and hemorrhage resulting in a hemorrhagic stroke.

In the past, it has been very difficult to treat a patient having a high risk wide-neck brain aneurysm condition. In the past, a surgical procedure to treat a brain aneurysm generally involved opening the skull and the clipping of the aneurysm shut. Surgical treatments available for a brain aneurysm are frequently quite limited. In addition, brain aneurysms may be located within areas of the brain where surgical procedures will likely result in severe complications for a patient. It is therefore desirable to provide the least intrusive procedure available for treatment of a brain aneurysm which utilizes the manipulation of a catheter into the aneurysm site for occluding the aneurysm without the necessity for surgery. In the past, balloons have been used to occlude an aneurysm site or sack. A problem with the use of balloons is the risk of over-inflation which may result in the rupture of the aneurysm.

Generally, a non-intrusive treatment of an aneurysm site involves the blockage of blood flow to the aneurysm. Devices which may be referred to as vaso occlusive devices are commonly deployed to the aneurysm site through the use of a catheter delivery apparatus or introducer. One example of an implantable vaso occlusive device is a wire coil identified as a Guglielmi electrolytically detachable coil (GDC coil) which may be formed of platinum and/or nickel-titanium alloy. Devices of this nature maybe found in U.S. Pat. Nos. 4,994,069; 6,059,779; 5,643,254; 5,423,829; 6,024,754; and 5,522,822 for example.

A Platinum coil may be delivered to a treatment site by a catheter or introducer. Following release of the coil from the catheter, the coil may assume a randomly shaped mass which substantially fills the body lumen and/or aneurysm. The coil may also be coated with fibers or include a braided fibrous element to promote clotting of the blood flow proximate to the treatment site.

Alternatively, the coil may typically be formed of a platinum/tungsten alloy coil. The coils may be formed of wire having a diameter of 2 to 30 mils and is preferably flexible and soft to minimize risk of herniation of an aneurysm to be treated.

Generally, following the placement of a coil within an aneurysm a thrombus forms in the aneurysm and is followed by a collagenous material reducing the risk of aneurysm rupture.

Alternatively, a predominately platinum coil may be placed within a wide-neck aneurysm where the coil may be severed from the insertion catheter by the application of a desired and relatively small level of electrical current. In this embodiment, the coil is engaged to a guidewire through an electrolytically detachable and/or dissolvable joint. Upon exposure to the small level of current the electrolytically dissolvable joint corrodes and fails separating the platinum coil from the delivery catheter. The guidewire and/or catheter is preferably formed of a steel material and therefore functions as an anode when exposed to electrical current. The coil is generally an effective cathode when in electric contact with most metals to facilitate galvanic electrolysis at the location of the dissolvable joint.

A potential complication to be addressed during the non-intrusive treatment of a wide-neck aneurysm is the prevention of migration of a coil from the interior of the aneurysm and into a parent vessel. A need therefore exists for a stent to be positioned adjacent to the neck of an aneurysm where the stent functions to block the coil from migration out of a vessel defect. In addition, a need also exists for a stent which may remain in contact with any size of platinum coil or platinum coil mass for prevention of migration while the stent simultaneously is immune from electrolytic corrosion.

A need therefore exists for a sacrificial anode stent system which partially occludes a wide-neck aneurysm while simultaneously stenting a blood vessel adjacent to an aneurysm which is susceptible to herniation and/or rupture. Further, a need exists for a sacrificial anode stent system which facilitates the retention of an implant such as a platinum coil within the interior of the wide-neck aneurysm to occlude a desired portion of a body lumen.

BRIEF DESCRIPTION OF THE INVENTION

The sacrificial anode stent system generally includes a vaso-occlusive device for use during interventional therapy and vascular surgery where the sacrificial anode stent system is adapted to be inserted into a portion of a vasculature for treatment of a body vessel such as an aneurysm. The vaso-occlusive device of the present invention is generally employed in combination with a support structure such as a stent, stent-graft, graft, and the like, all of which will henceforth be referred to by the term 'stent. The vaso-occlusive device is designed in such away that it may be readily anchored at the site of the vascular defect in combination with the support structure to minimize the migration of the device from a desired location. The support structure generally includes designated sacrificial anode portions utilized to minimize support structure degradation or corrosion during electrolytic detachment of the vaso-occlusive device from a delivery apparatus such as a catheter or introducer and thereafter when the device and the stent reside in the body.

The vaso-occlusive device of the present invention may include an occlusive member such as a platinum coil for positioning within a wide-neck aneurysm.

The support structure of the present invention may include a member having a first unexpanded configuration and a second expanded configuration, such as a stent or the like, which assists in the prevention of migration of the vasoocclusive device from the site of the vascular defect while simultaneously stenting a diseased blood vessel.

Generally, the vaso-occlusive device is prevented from migration from a vascular defect due to the positioning of undulating bands of the stent or the wall structure of the stent in general across the neck of a vascular aneurysm.

The vaso-occlusive device maybe positioned within a vascular defect such as an aneurysm by insertion of a catheter and/or guidewire, the device traversing through an opening in the sidewall of the stent.

The fluid flow-occluding device is generally formed of metal materials which may be platinum based for use as a cathode within in an electrolytic occluding device separation procedure.

The support structure may be formed of a variety of materials including but not necessarily limited to flexible polymeric materials and metallic materials which may embody shape memory materials, super elastic materials, as well as other materials which are bio compatible.

The sacrificial anode stent system may be employed in a procedure for treatment of vascular defects where blockage of the flow of fluid into an aneurysm and/or defective area of a vessel is desired.

In one embodiment the sacrificial anode stent system includes a support structure, namely a stent, which is positioned within a blood vessel traversing the neck of a vascular defect; a vaso-occlusive device, desirably in the form of a coil which is electrolytically detachable from a catheter and/or guidewire as positioned within the interior of the stent for traversal through a cell as defined by undulating bands within the stent; where the support stent includes one or more sacrificial electrolytically dissolvable sections functioning to prevent degradation of the undulating bands during electrolytic separation of the coil from the catheter/guidewire and thereafter as the stent and the vaso-occlusive reside in the body.

The support structures such as stents may include radiopaque markers which may be utilized to assist in the positioning of the stent proximate to an affected vessel wall. The radiopaque markers are generally secured to the distal ends of the stent extending outwardly from one or more peaks or troughs of undulating bands. One or more portions of sacrificial anode material maybe substituted for one or more of the radiopaque markers proximate to the distal ends of the stent. It is anticipated that the sacrificial anode materials will be adjacent to the radiopaque markers thereby redirecting any electrolytical corrosion of the sacrificial anode material and/or stent to a location away from the vascular defect and/or aneurysm. The radiopaque portions may include platinum, platinum-tungsten, palladium, platinum-iridium, rhodium, tantalum, or alloys or composites of these metals.

The coil which maybe utilized for positioning within an aneurysm is desirably compressed within a sheath prior to delivery to an aneurysm site. The coil is preferably sufficiently compressed for passing engagement through the interior of the stent for further traversal of the stent through either the gap between adjacent peaks and troughs of an undulating band or through an individual cell as defined by the undulating bands of the stent. The catheter including the coil may be manipulated for traversal of the stent into the wide-neck aneurysm site whereupon withdrawal or retraction of the sheath for release of the compressed coil may occur. The wide-neck aneurysm is thereby filled with the expanded coil for the occlusion of the vascular defect. An electrical current may then be applied to the catheter for corrosion of the coil at an area defined as the sacrificial catheter/coil joint for release of the coil from the catheter.

Prior to the separation of the coil from the catheter it is anticipated that the coil will be in contact with, and held in a desired position within a wide-neck aneurysm by, the undulating bands forming the wall of the stent. An electrical pathway is likely to occur between the coil and the stent upon the initiation of electrical current for corrosion of the sacrificial catheter/coil joint as a result of the probable contact between the coil and the undulating bands of the stent. An electrical pathway through the undulating bands to the distal ends of the stent is provided where the sacrificial anode material is engaged to the stent adjacent to the radiopaque markers. Corrosion of the undulating bands of the stent may therefore be redirected to a non-critical location adjacent to the radiopaque markers and away from any vascular defect subject to treatment.

In addition to the effect of occlusion of fluid flow, the sacrificial anode stent systems exhibits bio-compatibility, is efficient to manufacture, and may be deployed using known stent introduction techniques.

In one embodiment, the invention is directed to a sacrificial anode stent system comprising a stent having at least one sacrificial anode portion and a vaso-occlusive device. The vaso-occlusive device has at least one portion with a potential different from that of the sacrificial anode portion of the stent.

The invention is also directed to a sacrificial anode stent system comprising a stent and a medical device. The stent and the medical device each have at least one metal portion. The metal portion of the stent has a potential different from that of the medical device. One of the stent and the medical device includes a sacrificial portion of a different potential from that of the remainder of the stent or medical device. The potential of the sacrificial portion is such that corrosion occurs preferentially at the sacrificial portion.

The invention is also directed to a stent including at least one sacrificial anode portion. Typically, the sacrificial anode portion is connected to the stent proximate to the proximal and/or distal ends. Optionally, the sacrificial portion may be provided on one or more tabs extending from an end of the stent.

All United States patents and applications and other published documents mentioned anywhere within this application are incorporated herein by reference in their entirety.

Without limiting the scope of the invention other aspects and advantages of the invention will become apparent from the following detailed description and the accompanying drawings which illustrate by way of example the features of the invention. A brief abstract of the technical disclosure and the specification is provided as well for purposes of complying with 37 C.F.R. §1.72.

BRIEF DESCRIPTION OF THE SEVERAL VIEWS OF THE DRAWING(S)

Figure 2:
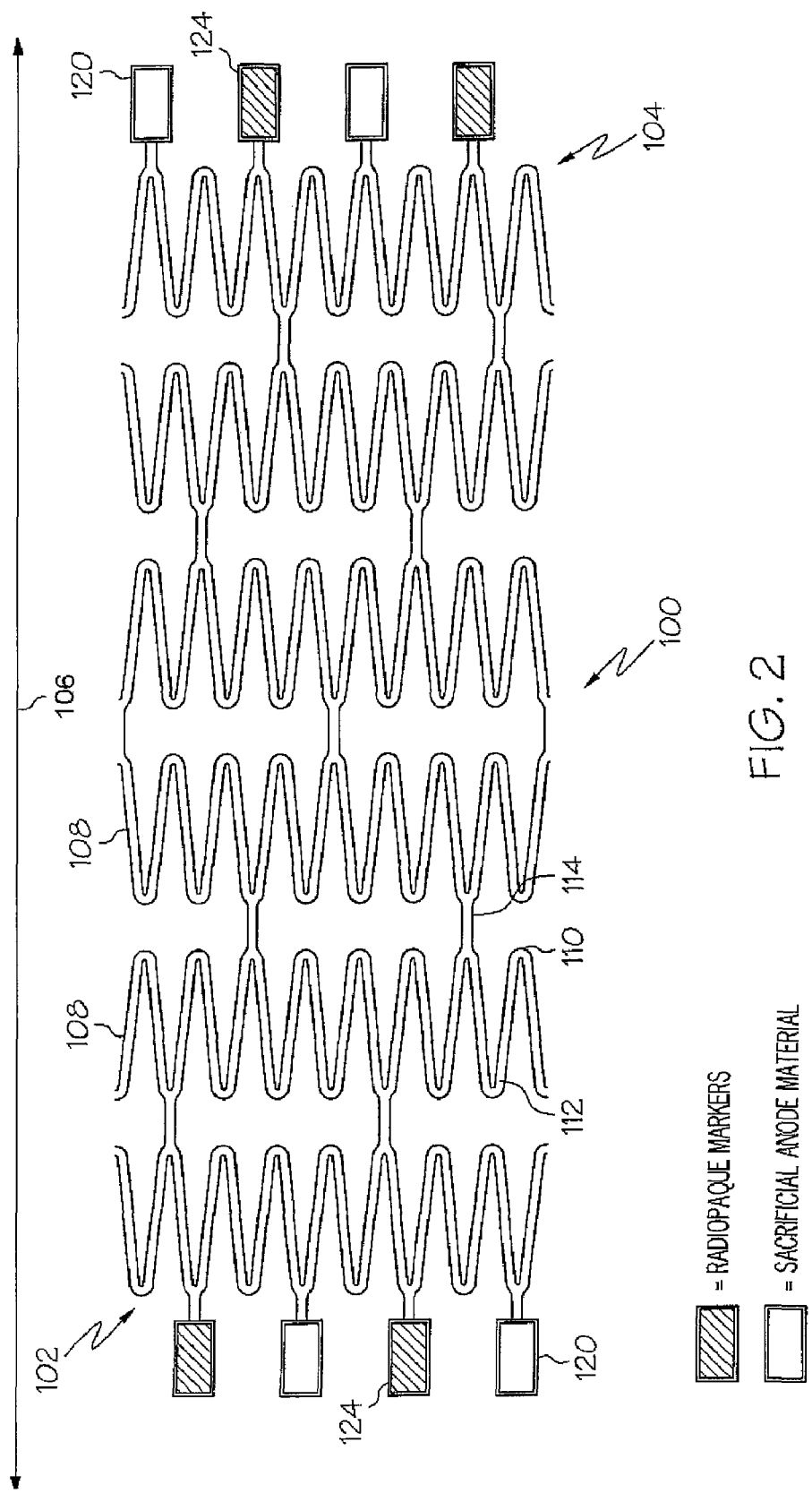
Figure 3:
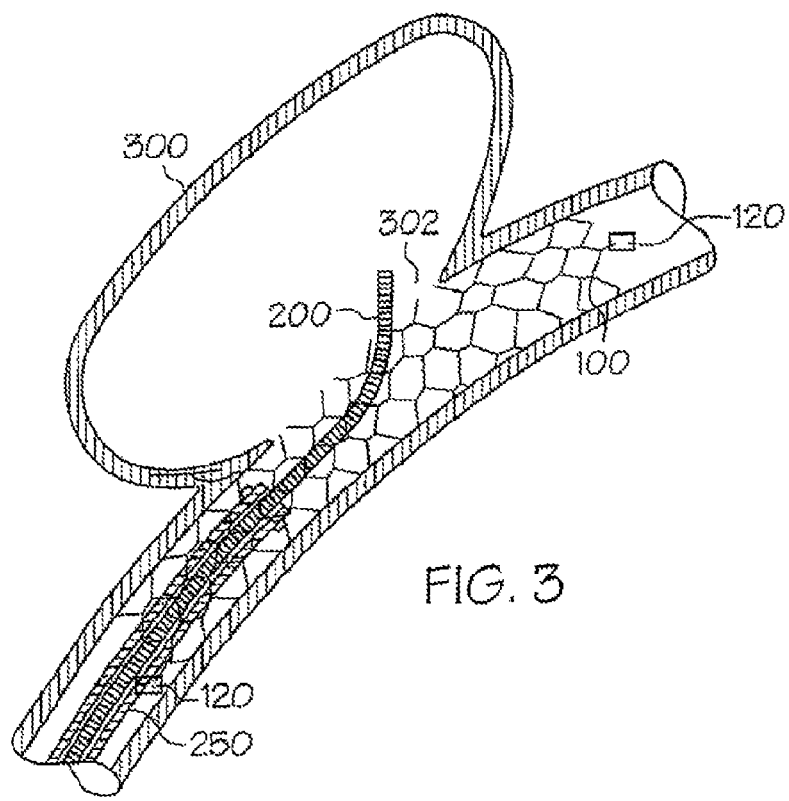
Figure 4:
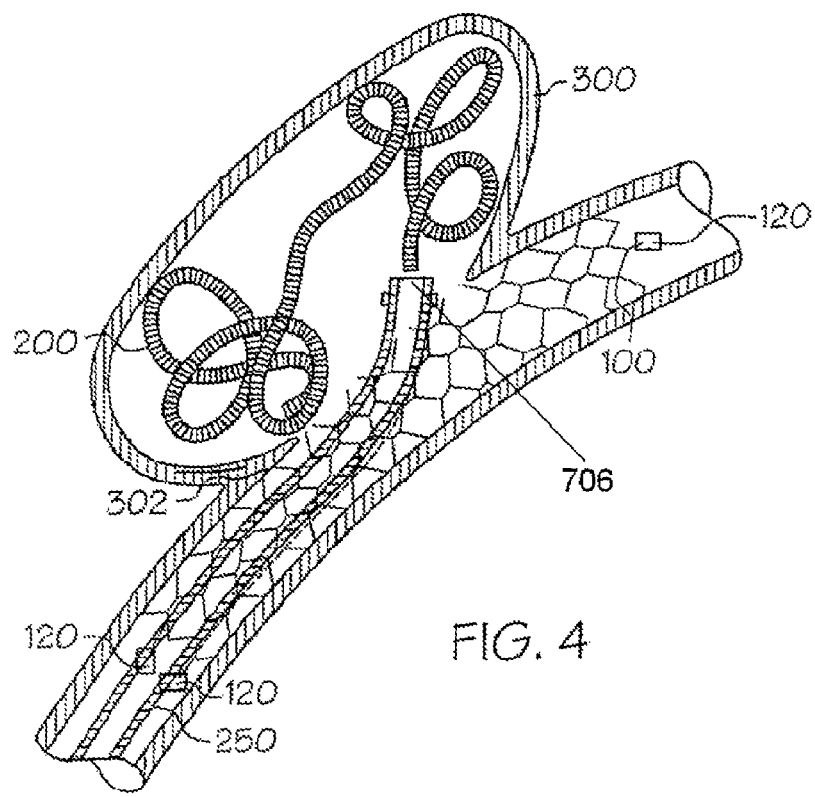

FIG. 1 shows an inventive sacrificial anode stent system.
FIG. 2 shows a flat pattern of an inventive stent.
FIGS. 3 and 4 show a coil being inserted into an aneurism.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different Figures refer to the same component.

The sacrificial anode stent system 10 generally includes a vascular support structure in the form of a stent 100. Non-limiting examples of stent which may be used in the instant invention are disclosed in U.S. patent application Ser. No. 09/957,983 which is incorporated herein by reference in its entirety. The sacrificial anode stent system 10 also generally utilizes a vaso-occlusive device such as a platinum coil 200 for positioning in a wide-neck aneurysm 300 as more fully described in U.S. Pat. Nos. 5,423,829; 5,643,254; 6,059,779; and 6,024,754 as assigned to Target Therapeutics, Inc., which are incorporated herein by reference in their entireties.

In more detail, the vascular support structure of the present invention, in one embodiment, is in the form of a stents having a wall surface with a plurality of openings therein. The stent may have a pattern such as those shown generally at 100 in FIG. 2 by way of example. Stent 100 has a proximal end 102, a distal end 104 and a flow path therethrough along a longitudinal axis 106. Stent 100 comprises a plurality of undulating bands 108. Each undulating band comprising a series of alternating peaks 110 and troughs 112. Peaks 110 are oriented in a distal direction and troughs 112 are oriented in a proximal direction. A plurality of connectors 114 extend between peaks 110 and troughs 112 of longitudinally adjacent undulating bands.

Stent 100 is also provided with a sacrificial anode portion 120. The sacrificial anode portion is a portion of the stent with a higher corrosion potential than the remainder of the stent. As shown in the embodiment of FIG. 2, the sacrificial anode portion 120 is in the form of tabs of metal at both ends of the stent. More generally, one or more sacrificial anode portions maybe provided at one or both ends of the stent or at any other suitable location in the stent. For example, the sacrificial anode portion may be in the form of additional material provided in the middle of the stent or anywhere else along the body of the stent. Desirably, however, the sacrificial anode portion of the stent is not necessary to the overall structural integrity of the stent and/or to the ability of the stent to support a vessel.

The sacrificial anode portion may be affixed to the stent via the use of adhesives, laser welding techniques or other welding techniques or swaged onto the stent. Other methods for incorporating the sacrificial anode portion into the stent include the use of various coating techniques including plating and vapor deposition techniques. The sacrificial anode portion may also be sprayed onto the appropriate portion of the stent or painted on.

The sacrificial anode portion may also be provided in the form of rivets of a higher potential metal which are disposed into openings in a stent.

The sacrificial anode stent system 10 also comprises one or more vasoocclusive devices 200, as shown in FIG. 1 which may be utilized to treat a wide-neck aneurysm 300.

Non-occlusive treatment of a wide-neck aneurysm 300 involves the positioning of a support structure which may be a stent 100 as earlier described to longitudinally traverse the neck 302 of the aneurysm 300.

The wall surface of the stent 100 may be used to partially occlude the neck of the aneurysm 302. The wall surface of stent 100 further functions to support a vaso-occlusive device. Desirably, the vaso-occlusive device is in the form of a coil. More desirably, it is in the form of a platinum coil or a Guglielmi electrolytically detachable coil (GDC coil) 200. A stent is disposed inside the wide-neck aneurysm 300 to assist in the prevention of herniation of the aneurysm and/or undesirable migration of coil 200 out of the aneurysm and into the parent vessel 400.

The coil 200 is generally formed of platinum which is an effective cathode with respect to most metals when exposed to an electrical charge. Typically, support structure 100 is formed of stainless steel, in the case of balloon expandable stents or nitinol in the case of self-expanding stents. Stainless steel and nitinol stents 100 function as an anode with respect to the coil 200 when in contact with one another in an electrolytic solution, as is present in the body. This renders the stent susceptible to electrolytic or galvanic corrosion deteriorating the integrity of the stent adjacent to a diseased vessel.

To avoid undesirable corrosion of the stent 100 proximate to a coil 200 or the like, the stent is provided with sacrificial anode portions 120 which redirect electrolytic galvanic corrosion to a desired non-critical location for the stent 100.

One or more sacrificial anode portions 120 may be provided. Desirably, the sacrificial anode portions will be positioned at one or both ends of the stent. In the embodiment of FIG. 2, sacrificial anode portions 120 are provided at both the proximal and distal ends of the stent.

The sacrificial anode portion 120 in another embodiment may be engaged to the stent 100 at any desired location so long as the corrosion/disintegration of the sacrificial anode portion 120 does not adversely affect the structural integrity of the sent 100 and particularly does not affect the structural integrity of the stent 100 adjacent to a vascular defect such as an aneurysm.

The sacrificial anode portions may be in the form of metal plated or coated onto a portion of the stent, or affixed, attached, or otherwise engaged to the stent. The sacrificial anode portions 120 are in electrical communication with the remainder of the stent 100 and have a higher corrosion potential than the remainder of stent 100.

Any suitable material maybe selected for the sacrificial anode portions 120 so long as the material has a higher corrosion potential than the remainder of the stent or support structure. Materials utilized for the sacrificial anode portion may include but are not necessarily limited to magnesium, zinc, aluminum, mild steel, low alloy steel, and/or iron. Desirably, the sacrificial anode portion will be made of mild steel, low alloy steel, zinc, aluminum, and magnesium.

Stents used in association with the sacrificial anode stent system are commonly formed of stainless steel. The stainless steel material for the stent is, in turn, a cathode with respect to the sacrificial anode portion. The materials selected for the sacrificial anode portion therefore function as an anode with respect to the cathotic stainless steel stent.

The range of materials available for functioning as the sacrificial anode material 120 is therefore quite large and are not limited to the materials identified within the specification. It is anticipated that any suitable metallic material may be utilized as the sacrificial anode portion 120 provided that the material selected has a higher corrosion potential than the remainder of the stent 100.

Platinum is generally the most cathotic, and has the lowest corrosion potential for materials selected for a coil 200. Therefore, platinum is likely to be the most widely used material as the coil for occlusion of an aneurysm.

The sacrificial anode portions 120 may generally be any size as desired for use in a medical procedure. It is anticipated that the sacrificial anode portions 120 will have size dimensions which will not exceed 0.016 inches in diameter; 0.003 inches for wall thickness; and 0.080 inches in length. Generally it is anticipated that the sacrificial anode portions 120 will be cylindrical in shape. Alternatively, the sacrificial anode portions 120 may be solid or have any other geometric shape as desired. The size and shape of the sacrificial anode portions 120 may vary considerably dependent upon the area of the body lumen to be non-invasively treated through the use of the sacrificial anode stent system 10.

The stent of FIG. 2 also includes optional end tabs which are utilized to fixedly secure radiopaque markers 124. The radiopaque markers 124 function to identify the location of the opposite ends of a stent 100 relative to a body lumen in order to facilitate desired positioning of the stent 100 adjacent to a vessel defect such as an aneurysm 300. One or more radiopaque markers maybe replaced by one or more sacrificial anode portions 120. The end tabs of the known stents 100 may then be utilized as the affixation sites for attachment of the sacrificial anode portions 120.

The use of designated sacrificial corrosion portions 120 prevents the stent from deteriorating and/or breaking proximate to a vascular defect minimizing risk of hemorrhage and/or rupture of the body lumen or aneurysm 300. The amount of sacrificial anode material 120 utilized should preferably be sufficient to remain intact for a desired duration of time to permit complete endothelialization of the stent. The amount of material utilized as the sacrificial anode portion 120 may be determined upon experimentation for identification of worse case corrosion rates for the combination of a given stent and coil.

The provision of sacrificial anode portions 120 prevents premature corrosion of the stent 100 and potential embolization of a wide-neck aneurysm 300 or vessel defect. The support structure/stent material and sacrificial anode portions 120 are therefore required to be selected for the combination of electrical parameters such that a higher corrosion potential exists for the sacrificial anode portion 120 following exposure to electrical current or galvanic electrolysis than the remainder of the stent 100. In addition, the combination materials selected for the support structure/stent and sacrificial anode portions 120 are required to be bio-compatible for use in treatment of vascular defects such as wide-necked aneurysms.

Electrolytic complications such as corrosion of critical portions of a stent are avoided by inclusion of sacrificial anode portions 120 in non-critical portions of the stent. The use of sacrificial anode portions 120 reduces the likelihood that a portion of the stent material exposed to corrosion will become liberated from the stent and enter the vasculature of an individual. Further, the use of sacrificial anode portions 120 minimizes the liberation of large particles separating from the stent at multiple electrolysis sites. The health and safety of an individual is thereby significantly enhanced.

A potential complication to be addressed by the sacrificial anode stent system 10 is the size of the diameter of the catheter relative to the size of the cell opening or gap between adjacent peaks and troughs of adjacent undulating bands forming the stent 100. In this instance an introducer which may be a catheter having a sheath or a guidewire within the catheter may be utilized for extension outwardly from the sheath for insertion of a coil 200 traversly through a cell or gap between the undulating bands of the stent for insertion into the wide-neck aneurysm.

In one embodiment, a coil 200 may be compacted and enclosed within a sheath of a catheter. In this instance the diameter of the catheter is sufficiently small for passing through an opening in the wall of the stent for introduction into a wide-neck aneurysm. Retraction of the sheath relative to the catheter exposes the coil 200 enabling further introduction of the coil 200 and expansion of the coil 200 within the wide-neck aneurysm to occlude the vascular defect.

In an alternative embodiment, a coil 200 may be enclosed within a sheath for delivery to an aneurysm site through the use of an introducer or catheter having a sheath. Prior to the introduction of the coil 200 into a wide-neck aneurysm the sheath may be retracted where only the coil 200 traverses the stent through a cell opening or through a gap between adjacent undulating bands.

In another embodiment, as shown in FIG. 3, a microcatheter 250 may be utilized as a delivery introducer for the coil 200 through the body lumen and stent for introduction into the wide-neck aneurysm. The microcatheter desirably easily passes through an opening in the wall surface of the stent for entry of the coil 200 into the vascular defect.

As may be seen in FIGS. 3 and 4, an initial treatment of an aneurysm 300 is shown. The aneurysm 300 includes a neck 302. A delivery catheter 250 delivers a coil 200, through the an opening in the sidewall of the stent into an aneurysm 300. Before the positioning of the catheter 250 as shown in FIG. 3, the catheter body may be guided by a guidewire that the distal tip of the catheter is within the aneurysm space. The guidewire may then be withdrawn to allow introduction of other vaso-occlusive material as described herein.

FIG. 4 shows a vaso-occlusive device 200 being ejected from the distal tip of the catheter. In this instance, the vaso-occlusive device 200 is shown to be a coil having secondary form which is generally somewhat random in nature. In this variation of the invention, the coil 200 may be coated with a polymeric composition. The coil 200 is generally introduced within the aneurysm space to substantially fill the space to promote occlusion.

Following introduction of the coil 200 within the aneurysm space, the delivery catheter may be withdrawn from the body lumen for termination of the non-invasive procedure.

Additional details of a coil 200 and the delivery thereof may be found in U.S. Pat. Nos. 4,994,069; 6,059,779; 5,643,254; 5,423,829; 6,024,754; and 5,522,822.

A platinum or Guglielmi detachable coil (GDC coil) is more desirable in that the physician may place the coil accurately in a final position within the selected site prior to releasing the coil through the use of electrolysis.

In the case where the vaso-occlusive device is a coil, the sacrificial anode portion 120 of the stent is desirably sufficiently large to avoid disintegration and/or detachment from the stent 100 prior to the disintegration of the coil 200 from an introducer which occurs at the location of a sacrificial joint in the delivery system.

The material selected for the sacrificial anode portion 120 has a higher corrosion potential than the primary support structure or stent 100. The material selected for the sacrificial anode portion 120 also has a lower corrosion potential than the sacrificial joint 706 between a coil 200 and an introducer.

Exposure of electrical current to the sacrificial anode stent system 10 thereby initiates corrosion/deterioration at the sacrificial joint simultaneously with the sacrificial anode portion 120. The material selected for the sacrificial joint corrodes more rapidly due to the sacrificial joint having a higher corrosion potential. The complete disintegration of the sacrificial joint between the coil 200 and an introducer therefore occurs prior to the complete corrosion and/or deterioration of the sacrificial anode portion 120.

An indicator maybe utilized to signal the separation of the coil 200 from an introducer for triggering of a switch to terminate the application of additional electrical current to the sacrificial anode stent system 10. Any excess current exposed to the sacrificial anode stent system 10 following separation of the coil 200 from the introducer thereby primarily affects the sacrificial anode portion 120 which in turn directs electrolytic corrosion away from critical areas of the stent 100.

The electrical current exposed to the support structure/stent 100 during separation of the coil 200 from the introducer causes minimal electrolytic or galvanic corrosion of the stent 100 due to the selection of a material for the stent 100 having a relatively low corrosion potential as compared to the sacrificial joint 706 and the sacrificial anode portion 120.

The integrity of the radiopaque markers 124 is generally not adversely affected by the application of electrical current to the sacrificial anode stent system 10. In an alternative embodiment where metallic materials have been utilized within the radiopaque markers 124, the metallic material selected has a corrosion potential which is lower than both the sacrificial joint 706 and sacrificial anode portions 120. Separation of the radiopaque markers 124 from the stent 100 is therefore prohibited.

The invention is also directed to a sacrificial anode stent system comprising a stent and a medical device, the stent and the medical device each having at least one metal portion, the metal portion of the stent having a potential different from that of the medical device, wherein one of the stent and the medical device includes a sacrificial portion of a different potential from that of the remainder of the stent or medical device, the potential of the sacrificial portion such that corrosion occurs preferentially at the sacrificial portion.

In one embodiment, the medical device is a coil and the sacrificial portion is part of the stent. The coil desirably includes platinum and the non-sacrificial portion of the stent desirably includes stainless steel although other combinations of metal may also be used. Most desirably, the sacrificial portion includes magnesium, zinc, aluminum, mild steel, low alloy steel, and/or iron.

In another embodiment, the sacrificial anode portion may be provided in the vaso-occlusive device. This would be appropriate where the choice of metals is such that the vaso-occlusive device would corrode more readily than the stent.

The invention is directed to the above-described sacrificial anode system and to methods of using the system in the treatment of patients as well as to inventive stents such as that shown in FIG. 2 having regions of sacrificial anode material. The design of the stent maybe modified in numerous ways as discussed below.

Bands of different amplitude and/or wavelength may be provided, as disclosed for example in U.S. application Ser. No. 09/957,983. Where serpentine bands are provided which are not characterized as having a wavelength and/or amplitude, different bands may have different numbers of peaks and troughs, as shown for example, in U.S. application Ser. No. 09/957,983. Bands of different longitudinal extent may also be provided as disclosed therein.

The connections between adjacent bands may be longitudinal or may be non-longitudinal. Examples of non-longitudinal connectors are disclosed in U.S. Pat. No. 6,348,065 and U.S. Pat. No. 5,922,021. Non-longitudinal connectors may be linear or may have one or more curved portions. Depending on the type of non-longitudinal connector, the ends of the connector may be circumferentially and longitudinally offset from one another as disclosed in U.S. Pat. No. 6,348,065 and U.S. Pat. No. 5,922,021.

Other designs may also be employed with the inventive stents. For example, a Palmaz design such as those disclosed in U.S. Pat. No. 4,776,337 may be modified by providing it with sacrificial anode material. In one embodiment, the sacrificial anode material would be provided on one or more tabs which extend from one or both ends of the stent.

The inventive stents disclosed herein may be of uniform wall thickness or may have different wall thicknesses in different portions of the stent. One end or both ends may be thicker than the middle of the stent or thinner than the middle of the stent. The thickness of the stent may increase from one end to the other end.

Regions of differing rigidity may be achieved by providing more connectors in one or more portions of the stent than in other portions. The rigidity may also be affected by changing the nature of the connectors in differing portions of the stent. For example, spiral connections between undulating bands or sections of the stent will result in more flexibility than straight connectors, given a constant spacing between the bands. Thicker or stronger material may also be used in one or more portions of the stent to provide additional rigidity to the stent. The stent may be provided with one or more ends of increased rigidity compared to the middle of the stent or with one or more ends of decreased rigidity compared to the middle of the stent.

The inventive stent may be of uniform cross-section or may exhibit a taper in one or both ends of the stent in the unexpanded and/or expanded configurations.

The inventive stent may also be in the form of a bifurcated stent.

As discussed above, any of the inventive stents disclosed herein may be provided with one or more radiopaque portions. The radiopaque portions may be provided in the form of a coating or plating or may be adhered to the stent mechanically or via welding. The radiopaque portion may also be swaged to the stent or provided in the form of a rivet. The ends of the stent may be provided with the radiopaque portion or any other desirable portion of the stent including the middle portion.

The inventive medical devices may also be provided with various biocompatible coatings to enhance various properties of the inventive medical devices. For example, the inventive medical devices may be provided with lubricious coatings or other polymeric coatings. An example of a suitable polymeric coating is PTFE, The inventive stents and/or coils disclosed herein may include one or more coatings which comprise one or more therapeutic agents, cellular materials, polymeric agents The therapeutic agent may be non-genetic or genetic. Suitable non-genetic therapeutic agents include anti-thrombogenic agents such as heparin, heparin derivatives, urokinase, and PPack (dextrophenylalanine proline arginine chloromethylketone), anti-proliferative agents such as enoxaprin, angiopeptin, or monoclonal antibodies capable of blocking smooth muscle cell proliferation, hirudin, and acetylsalicylic acid, anti-inflammatory agents such as dexamethasone, prednisolone, corticosterone, budesonide, estrogen, sulfasalazine, and mesalamine, antineoplastic/antiproliferative/anti-miotic agents such as paclitaxel, 5-fluorouracil, cisplatin, vinblastine, vincristine, epothilones, endostatin, angiostatin and thymidine kinase inhibitors, anesthetic agents such as lidocaine, bupivacaine, and ropivacaine, anti-coagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides, vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents; vasodilating agents; and agents which interfere with endogenous vascoactive mechanisms.

Suitable genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-I), BMP-8, BMP-9, BMP-10, BMP-1 1, BMP-12, BMP-13, BMP-14, BMP-15, and BMP-16. Any of BMP-2, BMP-3, BMP-4, BMP-5, BMP-6 and BMP-7 are particularly desirable. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Suitable cellular materials include cells of human origin (autologous or allogeneic) or from an animal source (xenogeneic), genetically engineered if desired to deliver proteins of interest at the transplant site. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAYHDROL®, etc.), fibrin, collagen and derivatives thereof, polysaccharides such as celluloses, starches, dextrans, alginates and derivatives, hyaluronic acid, squalene emulsions.

Desirably, polyacrylic acid, available as HYDROPLUS® (Boston Scientific Corporation, Natick, Mass.), and described in U.S. Pat. No. 5,091,205, the disclosure of which is hereby incorporated herein by reference, may be used. Also desirably, the polymer may be a copolymer of polylactic acid and polycaprolactone. Other materials include selected medical-grade biodegradable materials such as PGA-TMC, Tyrosine-Derived Polycarbonates and arylates, polycaprolaetone co butyl acrylate and other co polymers, Poly-L-lactic acid blends with DL-Lactic Acid, Poly(lactic acid-co-glycolic acid), polycaprolactone co PLA, polycaprolactone co butyl acrylate and other copolymers, Tyrosine-Derived Polycarbonates and arylate, poly amino acid, polyphosphazenes, polyiminocarbonates, polydimethyltrimethylcarbonates, biodegradable CA/PO$_4$'s, cyanoacrylate, 50/50 DLPLG, polydioxanone, polypropylene fumarate, or polydepsipeptides.

Other suitable coatings include macromolecules such as chitosan and Hydroxylpropylmethylcellulose. Surface erodible materials may also be used. Coatings may also comprise maleic anhydride copolymers, zinc-calcium phosphate and amorphous polyanhydricles.

The inventive medical devices may also be provided with a sugar or more generally a carbohydrate and/or a gelatin to maintain the inventive medical devices on a balloon during delivery of the medical device to a desired bodily location. Other suitable compounds for treating the inventive medical devices include biodegradable polymers and polymers which are dissolvable in bodily fluids. Portions of the interior and/or exterior of the inventive medical devices may be coated or impregnated with the compound. Mechanical retention devices may also be used to maintain the inventive medical devices on the balloon during delivery.

The inventive medical devices may also be provided in whole or in part with one or more of the above therapeutic agents, polymeric coatings or the like. Where multiple therapeutic agents are provided, the different coatings may release the drugs at different rates. For example, one therapeutic agent may be released at a fast rate and another therapeutic agent may be released at a slow rate. Where multiple polymeric coatings are provided, the coatings may degrade or erode at different rates.

Desirably, the sacrificial anode portions are not coated to a greater extent than the non-sacrificial anode portions to facilitate corrosion of the sacrificial anode portion rather than the remainder of the stent or other medical device.

The invention is also directed to other combinations of medical devices with sacrificial anode portions. For example, where a stent is used in combination with an implantable filter, for example, a vena cava filter, and the stent and implantable filter are made of different metals, one of the devices may be provided with a sacrificial implant portion, in accordance with the instant invention. The inventive stents and systems may find use in a variety of regions in the body including the coronary arteries, the peripheral arteries, arteries of the neck, cerebral arteries, veins, biliary ducts, urethras, ureters, fallopian tubes, bronchial tubes, the trachea, the esophagus, the prostate and bowels, or any other tubular organs. It is anticipated that the sacrificial anode stent system may be utilized for treatment of a cranial or brain aneurysm. The sacrificial anode stent system may also be used in the treatment of abdominal aortic aneurysms or other aneurysms within the body lumen.

In an alternative embodiment, the stent may be formed of more than one type of material where different portions of the stent are formed of different materials. In this embodiment, the sacrificial anode portion's 120 are required to have a higher corrosion potential than all materials selected for incorporation into the stent. The sacrificial anode portions 120 therefore function as anodes to redirect electrolytic corrosion away from the stent. The two or more materials incorporated into the stent in this embodiment are required to be in electric communication with each other to prevent electrical insulation and/or isolation of a particular material or area of the stent. The electric insulation and/or isolation within a particular area of the stent requires that the sacrificial anode portions 120 be in electric communication with each electrically independent portion of the stent. The electrical coupling of the sacrificial anode portions 120 to each electrically isolated portion of the stent facilitates redirection of any electrolytic corrosion away from the stent and vascular defect.

In another embodiment, two or more stents may be utilized within a procedure for treatment of a vessel defect. In this type of procedure a stent may be positioned within the interior of or adjacent to one or more additional stents. The material selected for the one or more additional stents may be identical or may be formed of different materials as required during a treatment procedure. In this embodiment, the two or more stents may be in contact and electrical communication with each other where only one stent is required to include the sacrificial anode portions 120. Alternatively, each stent may include one or more sacrificial anode portion's 120 to redirect electrolytic corrosion to a non-critical or desired location of the stent. In this embodiment, the sacrificial anode portions 120 generally have a higher corrosion potential than any and/or all of the materials selected for the one or more stents. Sacrificial anode portions 120 therefore function as sacrificial anodes with respect to the cathode of the stent and/or coil 200.

In yet another alternative embodiment a stent may be bifurcated where one arm or leg section is formed of one material and another section or leg is formed of a second material. If the two materials do not have sufficient electrical communication therebetween, one or more of the sections may include a sacrificial anode portion 120 having a higher corrosion potential than the respective section or leg of the stent. For example, one branch maybe formed of a different metal than the trunk, with the branch or trunk including a sacrificial anode portion.

In still another alternative embodiment, an aneurysm may be treated through the positioning of a coil 200 within the aneurysm and then the filling of the aneurysm with a liquid polymer mass which may be loaded with noble metal powder. It is anticipated that the noble metal powder will be in electric communication within a coil 200 and will simultaneously be in electric communication with the stent. The stent assists in the positioning and retention of the liquid polymer within the aneurysm. The sacrificial anode portions 120 in this embodiment preferably have a higher corrosion potential as compared to the stent, noble metal loaded polymer material, and the coil 200 to redirect electrolytic corrosion to the sacrificial anode portion's 120 and away from the noble metal powder, stent, or coil 200.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 maybe taken as alternatively dependent from claim 2; claim 4 may be taken as alternatively dependent on claim 2, or on claim 3; claim 5 may be taken as alternatively dependent on any of claims 2-4; claim 6 may be taken as alternatively dependent on any of claims 2-5; etc.).

The invention claimed is:

1. A sacrificial anode stent system comprising:
   a) a stent having at least one sacrificial anode portion and
   b) a vaso-occlusive device,
   the vaso-occlusive device having at least one portion with a potential different from that of the at least one sacrificial anode portion of the stent.

2. The sacrificial anode stent system of claim 1, wherein said at least one sacrificial anode portion is at a proximal or a distal end of the stent.

3. The sacrificial anode stent system of claim 1, the at least one sacrificial anode portion being a plurality of sacrificial anode portions.

4. The sacrificial anode stent system of claim 1, the at least one sacrificial anode portion being a plurality of sacrificial anode portions wherein said sacrificial anode portions are at a proximal and/or distal end of the stent.

5. The sacrificial anode stent system of claim 1, the at least one sacrificial anode portion being a plurality of sacrificial anode portions, the sacrificial anode portions provided in the form of tabs extending from one or both ends of the stent.

6. The sacrificial anode stent system of claim 5, wherein the stent further comprises radiopaque portions in the form of tabs extending from one or both ends of the stent.

7. The sacrificial anode stent system of claim 1, wherein the vaso-occlusive device is in the form of a coil.

8. The medical device of claim 7, wherein the coil includes platinum and the at least one portion with a potential different from that of the at least one sacrificial anode portion of the stent includes stainless steel.

9. The medical device of claim 8, wherein the at least one sacrificial anode portion is selected from the group consisting of magnesium, zinc, aluminum, mild steel, low alloy steel, and iron or any combination thereof.

10. The sacrificial anode stent system of claim 1, wherein the vaso-occlusive device is in the form of a Guglielmi coil.

11. A sacrificial anode stent system comprising:
    a) a stent and
    b) a medical device
    the stent and the medical device each having at least one metal portion, the at least one metal portion of the stent having a potential different from the at least one metal portion of the medical device, wherein the stent includes a sacrificial anode portion of a different potential from the at least one metal portion of the stent or medical device, the potential of the sacrificial anode portion such that corrosion occurs at the sacrificial anode portion.

12. The sacrificial anode portion stent system of claim 11, wherein the medical device is a coil.

13. The sacrificial anode stent system of claim 12, wherein the coil includes platinum and the at least one metal portion of the stent includes stainless steel.

14. The sacrificial anode stent system of claim 13, wherein the sacrificial anode portion is selected from the group consisting of magnesium, zinc, aluminum, mild steel, low alloy steel, and iron or any combination thereof.

15. A stent including at least one sacrificial anode portion.

16. The stent of claim 15, wherein the at least one sacrificial anode portion is connected to said stent proximate to said an end of the stent.

17. The stent of claim 15, further comprising a plurality of sacrificial anode portions connected to said stent.

18. The stent of claim 17, wherein the plurality of sacrificial anode portions are connected to said stent proximate to an end of the stent.

19. The stent of claim 15, wherein the at least one sacrificial anode portion is characterized by a higher potential than a remainder of the stent.

20. The stent of claim 15, wherein the at least one sacrificial anode portion is in the form of one or more tabs extending from a proximal or distal end of the stent.

* * * * *